United States Patent [19]

Colombo et al.

[11] 4,351,193
[45] Sep. 28, 1982

[54] SAMPLER FOR ANALYTICAL DETECTION SYSTEMS

[75] Inventors: Bruno Colombo, Cologno Monzese; Bruno Tosi, Carate Brianza, both of Italy

[73] Assignee: Carlo Erba Strumentazione S.p.A., Milan, Italy

[21] Appl. No.: 172,869

[22] Filed: Jul. 28, 1980

[30] Foreign Application Priority Data

Aug. 2, 1979 [IT] Italy ............................... 24861 A/79

[51] Int. Cl.³ ............................................. G01N 1/28
[52] U.S. Cl. .................................................. 73/864.82
[58] Field of Search ........... 73/864.81, 864.82, 864.83, 73/864.84, 863.73

[56] References Cited

U.S. PATENT DOCUMENTS

| | | | |
|---|---|---|---|
| 3,000,218 | 9/1961 | Marks et al. | 73/864.84 |
| 3,160,015 | 12/1964 | Charlton | 73/863.73 |
| 3,681,998 | 8/1972 | Karas | 73/863.73 |
| 3,933,165 | 1/1976 | Budzak | 73/863.73 |
| 4,055,259 | 10/1977 | Sibrava | 73/864.83 |

*Primary Examiner*—S. Clement Swisher
*Attorney, Agent, or Firm*—Lerner, David, Littenberg & Samuel

[57] ABSTRACT

The invention relates to a sampler for analytical detection systems, comprising a slide sealingly housed between two guide walls and movable to put a housing thereof from a sample receiving position to a sample delivering position and viceversa, said housing being washed by an inert gas into the sample receiving position in order to completely eliminate the environmental atmosphere from said housing notwithstanding such housing is opened to said atmosphere in the sample receiving position thereof.

14 Claims, 6 Drawing Figures

SAMPLER FOR ANALYTICAL DETECTION SYSTEMS

BACKGROUND OF THE INVENTION

1. Field of the Invention

This invention relates to a sampler, i.e. a device designed to carry out sampling, that is the introduction of samples into analytical detection system, said sampler comprising a housing for a sample to be analyzed, formed in a support movable from a position in which the sample is received to a position in which it is introduced into the analytical system, under perfect sealing, said housing being provided with at least one fitting tube to introduce an inert gas for sample washing.

2. Description of the Prior Art

Such samplers are already known in the art. A solid or liquid sample to be submitted to analysis for qualitative and quantitative determination of its components is introduced into them and then the sample introduction into the analytical detection system must obviously occur with the warranty that no other substance capable of altering detection and particularly air is introduced. Generally, these samplers are provided with a drum having several seats for samples, which are in turn positioned where each sample contained in its particular seat is injected into said housing, where it remains to be submitted to washing and is then introduced into the detection system. The known systems of this type generally provide ambient air elimination from the whole sampling system, including the drum with its various seats for samples, in such a way as to maintain the whole ambient under the influence of a washing inert gas, which is the same carrier gas as used in the analytical system. This system obviously requires particularly accurate, complex and expensive operations to obtain an environment, including all the samples to be analyzed, where any trace of atmosphere is eliminated. Furthermore, this involves a considerable loss of time, considering the time elapsing between the moment in which the sampler is loaded and the moment in which any trace of atmosphere has been eliminated from the whole unit and analysis can be finally started. In order to overcome these inconveniences, a sampler of the type described above has already been proposed, in an actual embodiment made by Carlo Erba Strumentazione S.p.A., in which a housing for a sample to be analyzed is obtained in a support movable under perfect sealing conditions within a seat, said support being movable to three different positions to receive the sample from the drum receptacles where the samples to be analyzed are contained, to allow sample washing operation and finally to introduce the sample into the analytical system. This embodiment allows to simplify the structure of sampler and also allows to eliminate dead times necessary to completely remove any residue of atmosphere from the sampler. However, this embodiment still shows some inconveniences, particularly due to the need of carrying-out said two-step displacement of removable support, from the position in which it receives the sample, to the position of washing and to the position of sample introduction into the analytical system, these steps being necessarily carried out with the outmost precision and while keeping the unit perfectly sealed to prevent ambient air from entering, even in very samll amounts, the analytical system. Moreover, this known system may give, in some cases, wrong indications due to air entrainment caused by the same movement of movable support.

SUMMARY OF THE INVENTION

An object of this invention is to provide a sampler for analytical systems of the above described type and improved in comparison with the lastly mentioned known embodiment, in that a motion step of the movable support is eliminated and at the same time a perfect sealing is ensured preventing even very small parts of atmosphere from entering the detection system.

According to the invention, this object is essentially achieved by designing the movable support as a slide moving under perfect sealing conditions within a seat with a two-position movement, in which the sample housing is aligned with a first seat opening, in contact with the atmosphere, to receive the sample and respectively with a second seat opening, insulated from the atmosphere, to introduce the sample into the analytical system, said slide seat further showing at least a tube for washing gas, connected with the slide seat when the slide is in its position aligned with said first opening.

In other words, it has been surprisingly noticed that, carrying out sample washing even when the slide is in the sample receiving position, in contact with the atmosphere, the characteristics of the washing gas are such as to ensure complete elimination of atmosphere from the whole slide seat, in such a way that the slide can then move to the position of injecting the sample into the analytical system without any consequence of ambient air entrainment. According to another particularly important feature of the invention, sealing from ambient air is ensured not only by mechanical systems of slide/seat coupling, but also by forming a screen of inert gas between the slide and seat walls on which the slide is designed to slip, by flowing said inert gas into a self-closed slot provided on each side of the slide in correspondence with the housing thereof.

DESCRIPTION OF THE PREFERRED EMBODIMENT

Figure 1:
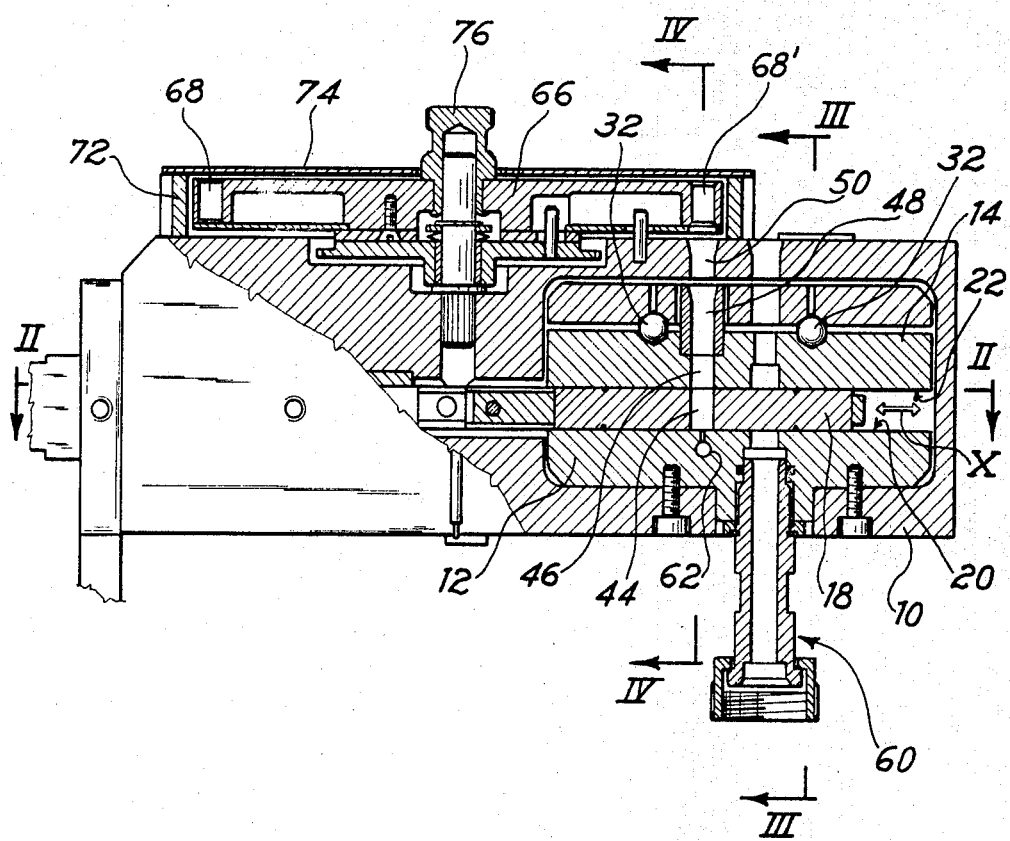
FIG. 1 is a side view with parts in section of a sampler according to a preferred embodiment of the invention.

With reference to the drawing, a support 10, for instance a metal one, houses the sampler, essentially consisting of a seat defined by a lower plate 12, an upper plate 14 and two slide guides 16, said plates and said guides defining an area in which a slide 18 is mounted capable of an alternate movement in the direction indicated by X in FIG. 1. The slide 18 is made of a suitable material, preferably antifriction plastic material or the like, for instance of self-lubricating type, and the surfaces 20 and 22 of plates 12 and 14 are appropriately lapped so as to allow perfect sealing when coupled with slide 18. Said two plates 12 and 14 are pressed under a maximum pressure of 3.5–4 $kg/cm^2$ by means of two or more bolts 24 (FIG. 3) which are fixed by nuts 26 in correspondence with the lower plate 12 and exercise a thrust on the upper plate 14 through Belleville washers 28 acting on a thrust plate 30, which in turn acts on the upper plate 14 through two or more spheric components 32 for stress distribution.

Figure 5:
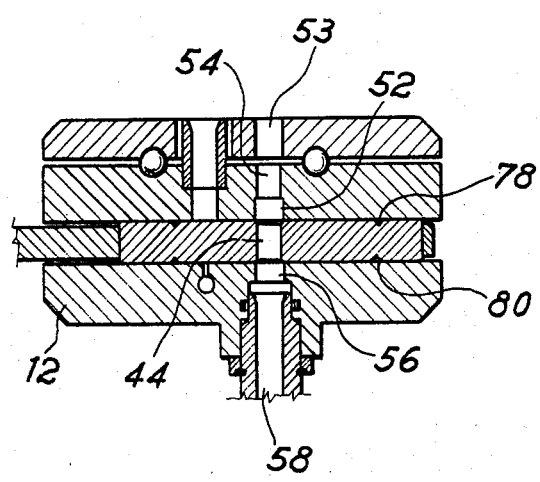
FIG. 5 is a partial cross-section showing the sampler slide, as illustrated in FIG. 1, but in its position of sample injection into the analytical detection system.

As already said, the slide 18 is movable in X direction between two positions: one to receive the sample, as shown in FIG. 1, and the other to inject the sample into the analytical system, as shown in FIG. 5. The slide movement is obtained thanks to the connection of same with a rod 34 of piston 36 appertaining to a cylinder-piston unit 38, for instance with fluidodynamic and double-acting control, the cylinder being fed through inlets 40 and 42.

The slide 18 shows a housing 44 where a sample to be analyzed is placed, said housing being vertically connected, in the position where the sample is received as shown in FIG. 1, to a series of openings 46, 48 and 50 in the upper plate 14, in the thrust plate 30 and in the support 10, so that a sample can fall through said aligned openings 50, 48 and 46, as far as inside the housing 44. An additional series of openings 52 and 53 is shown by plates 14 and 30 in correspondence with the second position of housing 44, as shown in FIG. 5, the opening 52 being closed by a sealing transparent cap 54 allowing to observe the sample falling into the analytical system and to check combustion occuring in it. Also the lower plate 12 presents, in alignement with the openings 52, 53 and 44, an opening 56 aligned with an inlet 58 through which the sample falls into the analytical detection system as indicated by its fitting tube 60.

Figure 2:
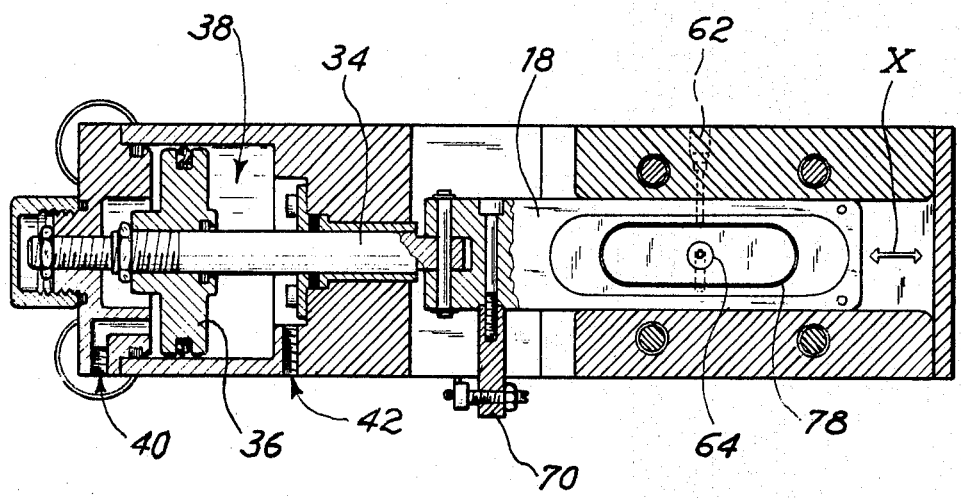
FIG. 2 is a section according to line II—II of FIG. 1.

As it can be particularly observed in FIGS. 1 and 2, the lower plate 12 has a tube 62 into which a washing inert gas is introduced, said tube, through an inlet 64 on the bottom of the housing 44, entering the housing itself to perform washing of sample contained in it. As already said, gas fed through tube 62 and inlet 64 is an inert gas and corresponds to the carrier gas of the analytical system to which the sampler is connected, generally said gas being constitued by helium. It has been surprisingly noticed that feeding inert gas as indicated, the washing operation being carried out in the position of slide 18 as shown in FIG. 1, is sufficient to eliminate any residue of atmosphere present in housing 44, as well as in openings 46, 48 and 50, in such a way that, despite said washing in performed in contact with atmosphere, analysis occurs with the highest reliability.

Figure 3:
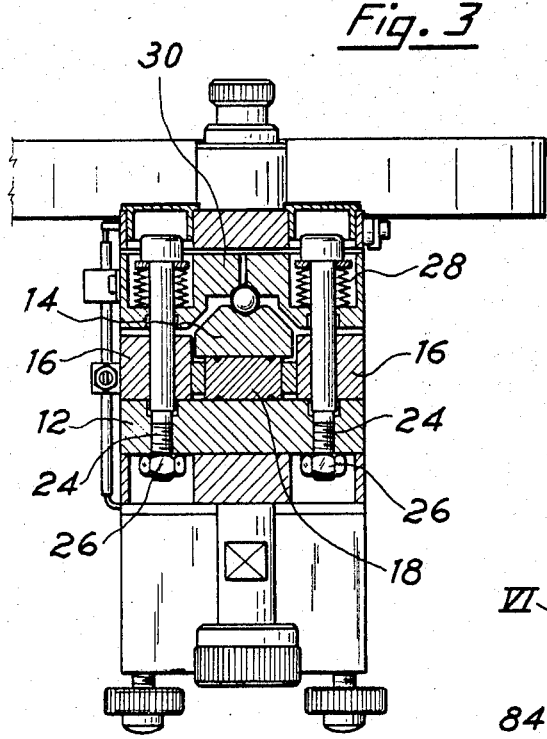
FIGS. 3 and 4 are cross-sections according to lines III—III and IV—IV of FIG. 1.
Figure 4:
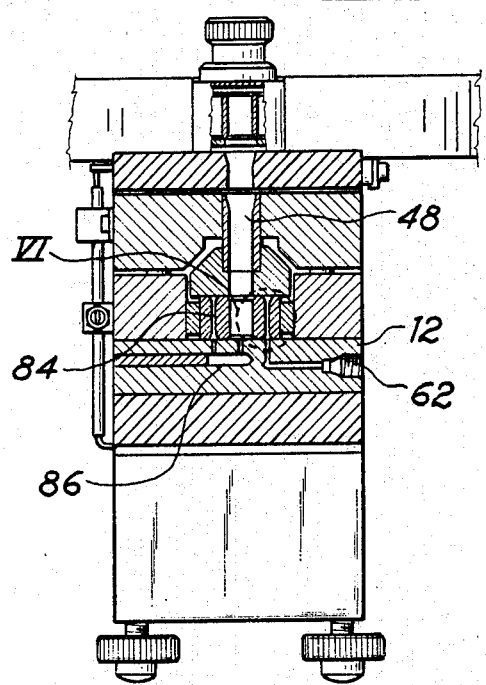

As can be noticed from FIGS. 1, 3 and 4, the support 10 bears a rotating drum 66 in which numerous holes 68 are formed each designed to contain a sample, said holes 68 being in turn positioned at 68' (FIG. 1) to let the sample fall into housing 44 through openings 50, 48 and 46. The necessary step-by-step advancement of drum 66 is driven by any known system, for instance a pawl actuated by an appendix 70 (FIG. 2) of slide 18. On the top of drum 66 and on an external circular crown 72 connected to the support 10, a cover 74 is provided, for instance of transparent plastic material, removably inserted through the central pivot 76 of drum 66. In such a way an environment is formed which, through not completely sealed from the atmosphere, is however gradually filled with the washing gas, namely helium, entering through tube 62 inlet 64, housing 44, openings 46, 48 and 50 and the area surrounding the drum 66, so that a kind of pre-washing of samples housed in seats 68 is carried out.

Figure 6:
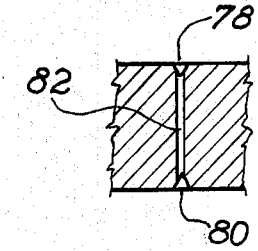
FIG. 6 is a partial cross-section on an enlarged scale showing a detail of the slide, as indicated by circle VI in FIG. 4.

According to an important feature of the invention, the upper and lower walls of slide 18 show a slot 78 and 80 respectively which is self-closed and has an elongated form as can be seen in FIG. 2, with a V section as shown in FIG. 6. Said slots 78 and 80 are placed around housing 44 and comprise both outlets of openings 46 and 56 in the two positions of slide 18, are in their turn connected to the inert gas supply in such a way as to form a shield to prevent blow-by of any even very slight amount of air into said openings and particularly into opening 56 due to any cause, including also the slide movement.

As it can be seen in detail in FIGS. 4 and 6, the tube 62 feeds the lower slot 80 which is on its turn connected to the upper slot 78 through a passage 82 in the slide body. From upper slot 78, said inert gas flows again into the lower slot 80 through another passage 84 and from slot 80 to a U-shaped channel 86 in the lower plate 12 to feed the inlet 64 of housing 44. In this way, elimination of any air molecule is in any case ensured, as it has been checked by so-called blank tests, i.e. performed without sample.

In an actual embodiment, the contact pressure recorded on the slide has been 3–3.5 kg/cm$^2$ and a housing 44 has been designed having a 6 mm diameter and 9 mm height, corresponding to the slide height, with washing capacity of 25 to 60 cc/min and an inlet 64 for washing fluid introduction into housing 44 of a diameter slightly less than 1 mm.

These data, however, can be modified and the details of the invention themselves can undergo modifications with respect to what has been previously illustrated, without in any case departing from the spirit and scope of the present invention.

We claim:

1. A sampler for transferring samples to analytical detection systems, said sampler comprising a slidable support having a support sample receptacle for receiving a sample to be analyzed and seat means engaging said slidable support for preventing atmospheric contamination of said sample during transfer, wherein said seat means has a first opening in contact with the atmosphere for passage of a sample into said support sample receptacle, said seat means has a second opening insulated from the atmosphere by said engagement for transfer of the sample from the support sample receptacle to the analytical system for analysis, and said seat means has at least one first inlet for introducing a protective gas, wherein said slidable support is movable between a first position in which the support sample receptacle is aligned with said first opening and a second position in which the support sample receptacle is aligned with said second opening, and wherein said slidable support and seat means define contact interfaces between the surfaces of said slidable support and said seat means having said openings and said support sample receptacle, and wherein said slidable support and seat means have at least one channel between each of said interfaces, said channels being in fluid communication with said first inlet, said channels being located so that they surround the support sample receptacle and said first and second openings when said slidable support is in both said first and second positions so as to provide means for the introduction of a fluid protective shield in the region between the engaging surfaces of said seat means and slidable support to avoid passage of air from the atmosphere between said engaging surfaces and thereby further prevent atmospheric contamination of said sample during transfer.

2. A sampler according to claim 1, wherein said slidable support is in the form of a body made of non porous antifriction material and said seat means comprises an upper wall and a lower wall between which said slidable support moves under sealing conditions, said walls having respectively said first and said second openings.

3. A sampler according to claim 2, wherein the upper and lower seat walls are submitted to a predetermined stress in a direction substantially perpendicular to the direction of movement of said slidable support.

4. A sampler according to claim 3, wherein said stress is exercised at least on one of said walls, through at least one load distribution spheric component.

5. A sampler according to claim 2, wherein the slidable support is driven reciprocally in two directions between said first and second positions by a two-position motor.

6. A sampler according to claim 2, wherein the surfaces of said slidable support in contact with said seat upper and lower walls have at least one channel, self-closed around the support sample receptacle.

7. A sampler according to claim 6, wherein said channels are longitudinal to the slidable support, and wherein the channel in the surface facing said upper wall surrounds said first opening when said slidable support is in both said first and said second positions, and wherein the channel in the surface facing said lower wall surrounds said second opening when said slidable support is in both said first and second positions.

8. A sampler according to claim 7, wherein said channels are pneumatically connected to each other through passages in the body of said slidable support as well as to a tube for said protective gas, through passages in the lower wall of the slidable support.

9. A sampler according to claim 2, wherein said second opening is axially aligned with an opening in the seat upper wall ahd hermetically sealed with transparent material to allow for a visual checking of sample injection into the analytical system.

10. A sampler according to claim 2, wherein a rotating drum, provided with drum sample receptacles for a predetermined number of samples, is mounted on top of the seat means and has a step-by-step advance means cooperating with the movement of the slidable support to align said drum sample receptacle sequentially with said support sample receptacle when said slidable support is in said first position so as to allow sequential transfer of individual samples from said drum to said slidable support and then from said slidable support to said analytical system.

11. A sampler according to claim 10, wherein said rotating drum is provided with a removable cover to allow access to said drum sample receptacles.

12. A sampler according to claim 1, wherein said seat includes a second inlet aligned with said first opening for introducing protective gas to support sample receptacle when said support sample receptacle is in said first position from the lower surface of said seat.

13. A sampler according to claim 12, wherein said first and second inlets are fluidically connected.

14. A sampler according to claim 2, wherein said first inlet is provided in said lower wall.

* * * * *